US010071361B2

(12) United States Patent
Osswald

(10) Patent No.: US 10,071,361 B2
(45) Date of Patent: Sep. 11, 2018

(54) FILTER MATERIAL FOR THE SELECTIVE REMOVAL OF SILOXANES

(71) Applicant: Dräger Safety AG & Co. KGaA, Lübeck (DE)

(72) Inventor: Jürgen Osswald, Hamburg (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 67 days.

(21) Appl. No.: 15/033,713

(22) PCT Filed: Oct. 29, 2014

(86) PCT No.: PCT/EP2014/002907
§ 371 (c)(1),
(2) Date: May 2, 2016

(87) PCT Pub. No.: WO2015/062723
PCT Pub. Date: May 7, 2015

(65) Prior Publication Data
US 2016/0279601 A1    Sep. 29, 2016

(30) Foreign Application Priority Data

Nov. 2, 2013 (DE) ........................ 10 2013 018 457

(51) Int. Cl.
| | |
|---|---|
| *B01D 53/04* | (2006.01) |
| *B01J 20/02* | (2006.01) |
| *B01J 20/22* | (2006.01) |
| *B01J 20/28* | (2006.01) |
| *B01J 20/32* | (2006.01) |
| *G01N 33/00* | (2006.01) |
| *B01D 39/02* | (2006.01) |
| *B01D 46/00* | (2006.01) |
| *B01J 20/30* | (2006.01) |
| *C07F 7/28* | (2006.01) |

(52) U.S. Cl.
CPC ............ *B01J 20/223* (2013.01); *B01D 39/02* (2013.01); *B01D 46/0036* (2013.01); *B01J 20/0211* (2013.01); *B01J 20/28038* (2013.01); *B01J 20/3085* (2013.01); *B01J 20/3204* (2013.01); *B01J 20/3231* (2013.01); *B01J 20/3236* (2013.01); *C07F 7/28* (2013.01); *G01N 33/0014* (2013.01); *G01N 33/0016* (2013.01)

(58) Field of Classification Search
CPC .. B01D 39/02; B01D 46/0036; B01J 20/0211; B01J 20/223; B01J 20/28038; B01J 20/3085; B01J 20/3204; B01J 20/3231; B01J 20/3236; C07F 7/28; G01N 33/0014; G01N 33/0016
USPC ....................... 95/90, 116, 900; 96/153–154; 502/400–401; 423/608–610
See application file for complete search history.

(56) References Cited

U.S. PATENT DOCUMENTS

| | | | | |
|---|---|---|---|---|
| 4,874,520 | A * | 10/1989 | Lee ...................... | B01D 15/325 |
| | | | | 210/198.2 |
| 6,630,062 | B1 | 10/2003 | Anderson et al. | |
| 7,795,173 | B2 * | 9/2010 | Vanderspurt ............ | A61L 9/205 |
| | | | | 423/610 |
| 2006/0144793 | A1 | 7/2006 | Dadachov | |
| 2007/0144961 | A1 * | 6/2007 | Tani .................. | B01D 53/8628 |
| | | | | 210/502.1 |
| 2008/0178738 | A1 * | 7/2008 | Chan .................. | B01D 53/8678 |
| | | | | 95/141 |
| 2009/0180941 | A1 * | 7/2009 | Vanderspurt ......... | B01D 53/885 |
| | | | | 423/210 |
| 2010/0120610 | A1 | 5/2010 | Schmidt et al. | |
| 2011/0052462 | A1 | 3/2011 | Schmidt et al. | |
| 2013/0142692 | A1 * | 6/2013 | Tarifi ...................... | A61L 9/205 |
| | | | | 422/4 |

FOREIGN PATENT DOCUMENTS

| | | |
|---|---|---|
| CN | 1721059 A | 1/2006 |
| CN | 101495212 A | 7/2009 |
| CN | 101778668 A | 7/2010 |
| CN | 101909696 A | 12/2010 |
| CN | 102491484 A | 6/2012 |
| DE | 197 41 498 A1 | 3/1999 |
| DE | 10 2010 032 619 A1 | 2/2012 |
| EP | 0 094 863 A1 | 11/1983 |
| JP | 2003-047831 A | 2/2003 |
| WO | 00/43765 A1 | 7/2000 |
| WO | 2007/143042 A2 | 12/2007 |

OTHER PUBLICATIONS

M. Ajhar et al., Bioresource Technology 2010, 101, 2913-2923.
Ren-De Sun et al: "Decomposition of gas-phase octamethyltrisiloxane on TiO2 thin film photocatalysts-catalytic activity, deactivation, and regeneration", Journal of Photochemistry and Photobiology A: Chemistry, vol. 154, No. 2, Nov. 7, 2002 (Nov. 7, 2002), pp. 203-209, XP055161909, ISSN: 1010-6030, DOI: 10.1016/S1010-6030(02)00322-2 Abschnitt. "2. Experimental"; p. 204, left-hand column—right hand column figures 2,5.
Koichi Kobayakawa et al: "Continuous-flow photoreactor packed with titanium dioxide immobilized on large silica gel beads to decompose oxalic acid in excess water", Journal of Photochemistry and Photobiology A: Chemistry, vol. 118, No. 1, Oct. 15, 1998 (Oct. 15, 1998), pp. 65-69, XP055162155, ISSN: 1010-6030, DOI: 10.1016/S1010-6030(98)00348-7 Abschnitt. "2. Experimental"; p. 65, right hand column figure 2.

(Continued)

*Primary Examiner* — Frank Lawrence
(74) *Attorney, Agent, or Firm* — McGlew and Tuttle, P.C.

(57) ABSTRACT

A filter material is for the selective removal of siloxanes from a gas. The filter material contains a titanium compound, which is an organotitanate and/or a compound, which can be obtained by hydrolysis of an organotitanate. A method for the production of the filter material is also provided to use the filter material for the selective removal of siloxanes from a gas. A gas sensor is provided which includes the filter material.

22 Claims, 1 Drawing Sheet

(56) References Cited

OTHER PUBLICATIONS

Titansaureester, Auszug aus Roempp Online, Version 3.37, Dec. 2007.

* cited by examiner

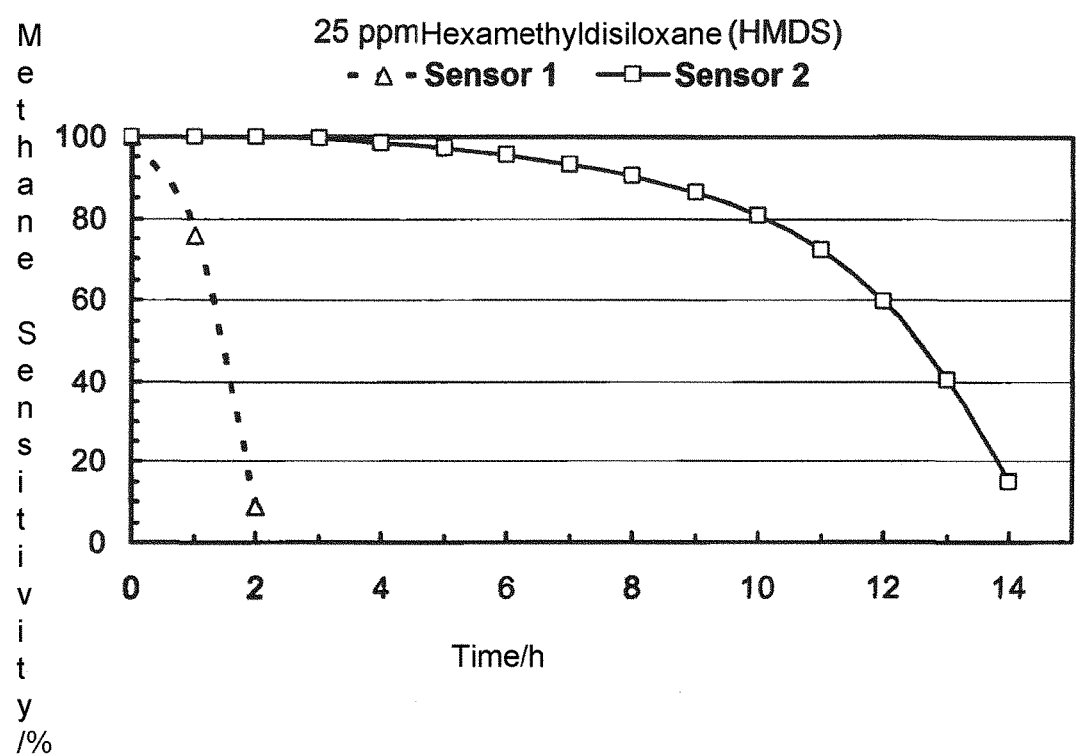

FILTER MATERIAL FOR THE SELECTIVE REMOVAL OF SILOXANES

CROSS REFERENCE TO RELATED APPLICATIONS

This application is a United States National Phase Application of International Application PCT/EP2014/002907 filed Oct. 29, 2014 and claims the benefit of priority under 35 U.S.C. § 119 of German Patent Application 10 2013 018 457.6 filed Nov. 2, 2013 the entire contents of which are incorporated herein by reference.

FIELD OF THE INVENTION

The present invention pertains to a filter material for the selective removal of siloxanes from a gas. The present invention further pertains to a method for the production of the filter material, to the use of the filter material for the selective removal of siloxanes from a gas as well as to a gas sensor which comprises the filter material.

BACKGROUND OF THE INVENTION

Siloxanes represent a widely used class of organic silicon compounds. They are oligomer or polymer compounds, in which adjacent silicon atoms are bridged by oxygen atoms and which typically have the general formula $R^1{}_3Si-O-[SiR^1{}_2O]_n-SiR^1{}_3$, in which $R^1$ independently represents hydrogen or alkyl. A typical representative of such siloxanes is hexamethyldisiloxane (HMDS).

Their extensive application possibilities and lack of toxicity are leading to an increasing widespread use of siloxanes. Siloxanes are used, for example, as components of dyes, paints, cosmetic articles, adhesives, impregnating agents and insulating agents and construction materials as well as auxiliary agents in the processing of plastics, and siloxane concentrations of a few ppb up to in the ppm range are often obtained because of the high vapor pressure of siloxanes in ambient atmosphere. In addition, siloxanes occur in said concentrations, for example, also as associated gas in biogas, sewage gas and landfill gas.

If siloxanes are involved in combustion processes, then silicon dioxide forms in this connection. The conversion of the siloxanes into silicon dioxide and the subsequent deposit thereof as solid can cause serious damage to technical equipment and measuring instruments.

For example, the presence of siloxanes in biogas and digester gas, which is used in the generation of energy by means of combustion, by means of the conversion to silicon dioxide and deposits resulting therefrom leads to damage to the combustion machines. For that reason, biogas has to be freed from siloxanes by means of a complicated treatment (M. Ajhar et al., Bioresource Technology 2010, 101, 2913-2923).

The forming of silicon dioxide may also lead to safety-relevant damage in gas sensors according to the heat tone principle or in so-called semiconductor sensors. If siloxanes are present in the gas atmosphere to be analyzed (e.g., in a plastics-processing factory or in a treatment plant), these are converted to silicon dioxide on the gas-sensitive layer of heat tone sensors and semiconductor sensors and the silicon dioxide is deposited on the gas-sensitive layer. The access of the analyte to the gas-sensitive layer is consequently hindered and the sensitivity of the gas sensor is reduced (so-called sensor toxification).

In case of a high siloxane load of the gas atmosphere to be analyzed, a reduction in the sensitivity of the sensor to half or even less can occur within a few hours because of this sensor toxification. The sensor can then no longer warn against an explosive atmosphere, or only to a limited extent. This is very precarious for safety reasons directly because of the usually long calibration interval of up to 3 months in some cases. A maintenance-intensive functional test must consequently be carried out more frequently in case of gas atmospheres loaded with siloxanes. Measuring sensors according to the heat tone principle or semiconductor principle must even be dispensed with entirely in case of very high loads and be switched to measuring principles (e.g., IR absorption) which are more cost-intensive and have drawbacks.

Therefore, various ways to remove siloxanes from gases have been pursued. Thus, the removal of siloxanes by means of condensation at a temperature of −25° C. is frequently carried out, for example, in the treatment of biogas. This method is, however, technically complicated and requires a great deal of energy for cooling to the necessary low temperature.

In some cases, adsorbers based on silica gel, highly disperse aluminum oxide, zeolites or activated carbons are also used in the treatment of biogas as well as in gas sensors. However, these materials bind siloxanes only weakly and unselectively. Very high absorber capacities must hence be provided to ensure that siloxanes are absorbed to a sufficient extent. Because of the low selectivity, this leads to other gas components also being absorbed, which leads to the loss of industrially exploitable gas components in industrial applications or the adulteration of the gas sample in analytical applications.

EP 0 094 863 A1 and WO 00/43765 A1 describe sensors for combustible gases according to the heat tone principle, in which the catalytically active sensor element is embedded in a porous absorbent material such as especially a zeolite material, as a result of which the sensor shall be insensitive to sensor toxins such as siloxanes. Nevertheless, it has been shown that the absorber material in such gas sensors reduces the diffusion rate of the gas to be analyzed, which leads to a reduced sensitivity, to a greatly prolonged response time and thus to a marked limitation of the detectable gases. As a rule, the response time and sensitivity of such sensors are only sufficient for methane and hydrogen, while higher alkanes such as propane and butane as well as other combustible substances can no longer be detected with certainty.

SUMMARY OF THE INVENTION

Thus, there is a need for gas sensors which are largely insensitive to the presence of siloxanes in the gas atmosphere to be analyzed and at the same time have a suitable sensitivity and response time especially for alkanes such as propane and butane. Furthermore, there is a need for filter materials, which make it possible to treat a gas sample or a gas stream by removing siloxanes for an industrial use or an analysis, with effects on the other components of the gas sample or of the gas stream being largely avoided.

This object is accomplished according to the present invention by a filter material for the selective removal of siloxanes from a gas, in which the filter material contains a titanium compound, which is an organotitanate and/or a compound, which can be obtained by hydrolysis of an organotitanate.

It has been surprisingly shown that the filter material according to the present invention shows high affinity and selectivity for siloxanes, for example, hexamethyldisiloxane and hence is outstandingly suitable for the selective removal of siloxanes from a gas sample or from a gas stream without any excessive effects on the other components thereof. In particular, the filter material according to the present invention is suitable to protect gas sensors, for example, according to the heat tone principle or so-called semiconductor sensors against a sensor toxification caused by siloxanes by means of the selective removal of siloxanes and at the same time to guarantee a sufficient sensitivity and response time for alkanes such as propane and butane as well.

The filter material according to the present invention contains at least one titanium compound, which is an organotitanate and/or a compound, which can be obtained by partial or complete hydrolysis of an organotitanate, for the selective binding of siloxanes.

Derivatives of orthotitanic acid $H_4TiO_4$ are particularly possible as organotitanates. Organotitanates of the formula $Ti(OR)_4$, in which R in each case independently represents hydrogen or a hydrocarbon group with 1 to 10 carbon atoms, with at least one R being the hydrocarbon group. Each of the hydrocarbon groups being optionally interrupted by one or more —O—, —NH—, —N= and/or —C(O)— and/or being substituted by one or more —OH and/or $NH_2$ and optionally two or three of the hydrocarbon groups being linked together forming a monocyclic or bicyclic ring, are preferred. The hydrocarbon group in this case is selected from straight-chain, branched or cyclic hydrocarbon groups. Furthermore, each of the straight-chain, branched or cyclic hydrocarbon groups is selected from saturated, unsaturated and aromatic hydrocarbon groups. In other words, organotitanates of the formula $Ti(OR)_4$, in which R in each case independently represents hydrogen or a hydrocarbon group with 1 to 10 carbon atoms with at least one R being the hydrocarbon group, and in which each of the hydrocarbon groups is interrupted by one or more —O—, —N— and/or —C(O)—, are preferred. Organotitanates of the formula $Ti(OR)_4$, in which R in each case independently represents hydrogen or a hydrocarbon group with 1 to 10 carbon atoms with at least one R being the hydrocarbon group, and in which two or three of the hydrocarbon groups are linked together forming a monocyclic or bicyclic ring, are also preferred. Organotitanates of the formula $Ti(OR)_4$, in which R in each case independently represents hydrogen or a hydrocarbon group with 1 to 10 carbon atoms with at least one R being the hydrocarbon group, each of the hydrocarbon groups being interrupted by one or more —O—, —N— and/or —C(O)— and two or three of the hydrocarbon groups being linked together forming a monocylic or bicyclic ring, are especially preferred.

In one embodiment, at least one of the R groups represents a hydrocarbon group with 2 to 10 carbon atoms, which is interrupted by one or more —O—, —NH—, —N= and/or —C(O)— and/or is substituted by one or more —OH and/or $NH_2$. In another embodiment, at least two of the R groups represent hydrocarbon groups, which are linked together forming a monocylic or bicyclic ring. In another embodiment, R in each case independently represents hydrogen or a straight-chain, branched or cyclic hydrocarbon group with 1 to 10, especially 1 to 6 and preferably 1 to 4 carbon atoms, the hydrocarbon groups being preferably not interrupted, substituted or linked together with at least one R being the hydrocarbon group. In a preferred embodiment, R in each case represents a straight-chain or branched saturated hydrocarbon group with 1 to 10, especially 1 to 6 and preferably 1 to 4 carbon atoms or an aromatic hydrocarbon group with 6 to 10 carbon atoms.

Tetraalkyl titanates and tetraaryl titanates are especially preferred.

In a preferred embodiment, the organotitanate is selected from the group consisting of tetramethyl titanate, tetraethyl titanate, tetra-n-propyl titanate, tetraisopropyl titanate, tetra-n-butyl titanate, tetra-tert-butyl titanate, tetra-n-hexyl titanate, di-isopropyl-di-n-butyl titanate, tetraphenyl titanate, titanium bis(triethanolamine)-diisopropoxide, titanium bis(triethanolamine)-di-n-butoxide, titanium (triethanolaminato)-isopropoxide, titanium bis(acetylacetonate)-diisopropoxide, titanium bis-(acetylacetonate)-di-n-butoxide and mixtures thereof. The organotitanate selected from the group consisting of tetraisopropyl titanate, tetra-n-butyl titanate and mixtures thereof is most preferred.

The titanium compounds according to the present invention are generally Lewis acid compounds. Examples of compounds, which can be obtained by the partial hydrolysis of an organotitanate, are compounds of the formulas $Ti(OH)(OR)_3$, $Ti(OH)_2(OR)_2$, $TiO(OR)_2$, $Ti(OH)_3OR$ and $TiO(OH)OR$, in which R in each case independently has the meanings defined above. Examples of compounds, which can be obtained by complete hydrolysis of an organotitanate, are titanium oxides, titanium hydroxides and titanium oxide hydrates. The filter material according to the present invention preferably contains mixtures of titanium compounds that can be obtained by partial and/or complete hydrolysis of one or more organotitanates according to the present invention. Without limiting to a certain theory, it is assumed that such mixtures of titanium compounds, which preferably contain titanium oxides, titanium hydroxides, titanium oxide hydroxides, titanium oxide hydrates and/or partially hydrolyzed organotitanates, are especially suitable for the selective binding of siloxanes.

It is preferred that the filter material according to the present invention contains approximately 10 wt. % to approximately 55 wt. %, especially approximately 15 wt. % to approximately 50 wt. %, preferably approximately 20 wt. % to approximately 45 wt. %, preferably approximately 30 wt. % to approximately 40 wt. % and especially preferably approximately 35 wt. % of titanium compound, calculated as titanium, in relation to the overall weight of the filter material.

The filter material according to the present invention preferably, further, contains a carrier. Usually, it is an inert carrier and especially a carrier, which is essentially inert to siloxanes. In this connection, it is preferred that the at least one titanium compound according to the present invention is applied to the carrier, especially in finely dispersed form, and the carrier is especially preferably coated with the at least one titanium compound according to the present invention.

In one embodiment, the carrier is a porous or preferably fibrous carrier and especially a mat. It is preferred, furthermore, that the carrier consists of glass fibers. The carrier is especially preferably a glass fiber mat.

In another embodiment, the carrier is a particulate carrier, especially a porous particulate carrier and preferably a carrier in the form of powder, granules, pellets or porous spheres. In this case, the filter material is preferably present in pourable form. Such a pourable material can be introduced into the gas inlet of a sensor or even into the volume flow of a biogas treatment plant in an especially simple manner.

It is therefore recognized that a filter according to the present invention may consist, for example, of a glass fiber mat, which is coated with an above-described filter material. It is also conceivable here that such a filter consists of a porous, particulate carrier, which is coated with an above-described filter material. It is also conceivable that the filter is a particulate filter, the particles of which are present, for example, in the form of powder, granules, pellets and porous spheres and consist of a mixture of the carrier material and of a filter material as described above.

Furthermore, it is preferred that the filter material according to the present invention contains approximately 10 wt. % to approximately 80 wt. %, especially approximately 15 wt. % to approximately 60 wt. %, preferably approximately 20 wt. % to approximately 50 wt. %, preferably approximately 30 wt. % to approximately 45 wt. % and especially preferably approximately 40 wt. % of carrier, in relation to the overall weight of the filter material.

The filter material according to the present invention may, moreover, contain suitable auxiliary agents. Examples of suitable auxiliary agents are surfactants. These can improve, for example, the wetting of a carrier with the titanium compounds according to the present invention. Furthermore, aluminum compounds such as aluminum distearate or aluminum-tri-(sec-butylate) are possible as auxiliary agents. Such aluminum compounds may contribute to a uniform application of the titanium compounds according to the present invention to a carrier. In a preferred embodiment, the filter material contains approximately 0.05 wt. % to approximately 2 wt. % and especially approximately 0.1 wt. % to approximately 1 wt. % of auxiliary agents, in relation to the overall weight of the filter material.

In other words, it is advantageous when the filter material is a composition of a titanium compound that is an organotitanate and/or a compound that can be obtained by hydrolysis of an organotitanate; a carrier, for example, a glass fiber mat or a porous particulate carrier; and/or an auxiliary agent, for example, a surfactant or an aluminum compound. In this connection, it is especially favorable when the filter material contains approximately 10 wt. % to approximately 80 wt. % of carrier in relation to the overall weight, when the filter material according to the present invention contains titanium compound(s) and carrier in an overall quantity of at least 90 wt. % in relation to the overall weight and/or when the portion of the titanium compounds (calculated as titanium) is approximately 10 wt. % to approximately 55 wt. % in relation to the overall weight of the filter material.

In a preferred embodiment, the filter material according to the present invention contains titanium compound(s) and carrier(s) in an overall quantity of at least 90 wt. %, especially at least approximately 95 wt. %, preferably at least approximately 98 wt. % and especially preferably at least approximately 99 wt. %. In a preferred embodiment, the filter material according to the present invention essentially or completely consists of the at least one titanium compound according to the present invention and carrier(s) as well as possibly auxiliary agents.

In an especially preferred embodiment, the filter material according to the present invention consists of a porous or preferably fibrous carrier, especially a glass fiber mat, which is coated with the at least one titanium compound according to the present invention as well as possibly auxiliary agents. In another especially preferred embodiment, the filter material according to the present invention consists of a particulate carrier, to which the at least one titanium compound according to the present invention as well as possibly auxiliary agents, especially in finely dispersed form, are applied.

The present invention also pertains to a method for the production of the filter material according to the present invention. In this case, a method, in which a) a solution of the organotitanate and/or a compound, which can be obtained by hydrolysis of an organotitanate, is applied in a solvent to a carrier,
b) the carrier is dried, and
c) the filter material is possibly subjected to a conditioning, is preferred.

In principle, any solvent, which has a sufficient solubility for the organotitanate used, may be used as a solvent. Isopropyl alcohol or toluene is preferably used as a solvent. Preferably, the solution of the organotitanate is applied to the carrier at a high temperature, especially at a temperature of approximately 30° C. to approximately 90° C., preferably approximately 40° C. to approximately 80° C., preferably approximately 50° C. to approximately 70° C. and most preferably at approximately 60° C.

The drying of the carrier is preferably carried out at a high temperature, especially at a temperature of approximately 30° C. to approximately 90° C., preferably approximately 40° C. to approximately 80° C., preferably approximately 50° C. to approximately 70° C. and most preferably at approximately 60° C. The drying is preferably carried out for a period of approximately 1 hr. to 72 hr., especially approximately 6 hr. to approximately 48 hr., preferably approximately 12 hr. to approximately 36 hr. and preferably approximately 24 hr. In a preferred embodiment, the drying is carried out in an atmosphere with no more than approximately 50%, especially no more than approximately 30%, preferably no more than approximately 20% and preferably no more than approximately 10% relative humidity and especially preferably essentially or completely in the absence of moisture.

A conditioning of the filter material is preferably carried out after the drying or simultaneously with the drying. This is usually carried out in ambient air or preferably in the presence of water vapor and especially preferably in a saturated water vapor atmosphere. The conditioning of the filter material is preferably carried out at a high temperature, especially at a temperature of approximately 30° C. to approximately 90° C., preferably approximately 40° C. to approximately 80° C., preferably approximately 50° C. to approximately 70° C. and most preferably at approximately 60° C. It is further preferred that the conditioning is carried out for a period of approximately 1 hr. to approximately 120 hr., especially approximately 24 hr. to approximately 120 hr., preferably approximately 48 hr. to approximately 96 hr. and preferably approximately 72 hr.

According to another embodiment, a filter material according to the present invention can also be obtained by a solution of the organotitanate being mixed in a solvent as described above and the precipitate thus obtained being isolated and being preferably applied to a carrier, as described above, especially in finely dispersed form.

The present invention further pertains to a filter material which can be obtained by the method according to the present invention. In this case, the preferred embodiments of the filter material according to the present invention and of the method according to the present invention defined above are preferred.

The present invention especially pertains to a filter material, which contains a titanium compound, the filter material being prepared by a solution of an organotitanate or a compound, which can be obtained by hydrolysis of an organotitanate, being applied to a carrier in a solvent, and the carrier being dried.

Furthermore, the present invention pertains to the use of a filter material according to the present invention for the selective removal of siloxanes from a gas. In this case, the preferred embodiments of the filter material according to the present invention defined above are preferred for the use thereof as well. The filter material according to the present invention is especially suitable for use in a method for the selective removal of siloxanes from a gas, in which the gas is passed through the filter material. In this case, it is especially preferred that the gas and the filter material have a temperature in the range of approximately −20° C. to approximately 60° C., especially approximately −10° C. to approximately 40° C. and preferably 0° C. to approximately 30° C. and especially preferably ambient temperature.

The present invention likewise pertains to the use of a titanium compound according to the present invention, especially a titanium compound that is an organotitanate and/or a compound, which can be obtained by partial or complete hydrolysis of an organotitanate, for the selective removal of siloxanes from a gas. In this case, the preferred embodiments of the titanium compound according to the present invention defined above are also preferred for the use thereof.

The present invention also pertains to a gas sensor, which comprises a filter material according to the present invention. It is preferably a gas sensor according to the heat tone principle, and especially a Pellistor, or a semiconductor sensor, especially a metal oxide semiconductor gas sensor. The filter material is usually introduced into the gas inlet of the sensor especially on a porous or fibrous carrier, such as a glass fiber mat or on a particulate carrier in the form of a bed. It is preferred that the quantity of titanium compound, calculated as titanium, is approximately 0.1 mg/cm$^2$ to approximately 100.0 mg/cm$^2$, especially approximately 1.0 mg/cm$^2$ to approximately 25.0 mg/cm$^2$, preferably approximately 4.0 mg/cm$^2$ to approximately 16.0 mg/cm$^2$, preferably approximately 8.0 mg/cm$^2$ to approximately 12.0 mg/cm$^2$ and especially preferably approximately 10.0 mg/cm$^2$ in relation to the gas inlet area of the gas sensor. Further preferred embodiments of the gas sensor according to the present invention are defined as above for the filter material according to the present invention.

Because of the high affinity and selectivity of the filter material according to the present invention for siloxanes, relatively small quantities of filter material at the gas inlet of a sensor are already sufficient to protect the sensor against toxification by siloxanes. In this case, by contrast to gas filters based on known absorber materials, the entry of gases such as hydrogen or methane and especially of propane and butane into the sensor chamber is not noticeably hindered such that at most slightly prolonged response times are observed for these gases. By using the filter material according to the present invention, gas sensors, for example, according to the heat tone principle, can therefore be used for determining gases from the series of alkanes, including butane or pentane in siloxane-containing atmospheres and thus for monitoring siloxane-containing, explosive environments.

The present invention is explained in detail below on the basis of examples as well as FIG. 1. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a graph showing a decrease in the methane sensitivity of two sensors, in case of admission of 25 ppm of hexamethyldisiloxane (HMDS). Sensor 1 (Δ) is a conventional sensor in this case, while sensor 2 (□) is a sensor with a filter according to the present invention.

DESCRIPTION OF EXEMPLARY EMBODIMENTS

Example 1

Tetraisopropyl titanate (3 g) was dissolved in isopropyl alcohol (10 mL) under reflux. The solution was subsequently cooled to approximately 60° C. and a glass fiber mat (25 mg, surface approximately 2 cm$^2$) was impregnated with it, approximately 0.5 mL of the solution being applied to the glass fiber mat. The freshly impregnated mat was dried for one day at 60° C. The conditioning was carried out by storing in a saturated water vapor atmosphere for three days at 60° C. The mat was subsequently dried again and arranged in the gas inlet of a heat tone sensor.

Example 2

Heat tone sensors without a gas filter (sensor 1, reference) or with a filter material as obtained in Example 1 in the gas inlet, which contained approximately 100 mg up to 150 mg of titanium compound, calculated as titanium (sensor 2), were exposed to an air stream, which contained in each case 50% LEL (lower explosive limit) hydrogen, methane, propane and n-hexane. Based on EN 60079, the gas sensitivity in mV/% LEL as well as the response time $t_{50}$ (i.e., the time, within which 50% of the final value was reached, also called the setting time) in seconds were determined in each case. The values obtained are shown in the following table.
Sensor 1: Heat tone sensor without gas filter (reference)
Sensor 2: Heat tone sensor with filter material according to the present invention

| Gas | Gas sensitivity (mV/% LEL) | | Response time $t_{50}$ (sec) | |
|---|---|---|---|---|
| | Sensor 1 | Sensor 2 | Sensor 1 | Sensor 2 |
| Hydrogen | 1.7 | 1.6 | 3 | 3 |
| Methane | 1.6 | 1.7 | 6 | 6 |
| Propane | 0.8 | 0.9 | 7 | 8 |
| n-Hexane | 0.7 | 0.7 | 8 | 42 |

These values show that the filter material according to the present invention does not bring about any noticeable reduction in the sensitivity for all gases analyzed and, in addition, the response time is only slightly prolonged even for propane. As a result, a gas sensor with the filter material prepared in Example 1 can be used for the determination of alkanes, including especially propane and even n-hexane.

Example 3

Heat tone sensors without a gas filter (sensor 1, reference) or with a filter material as obtained in Example 1 in the gas inlet, which contained approximately 100 mg to 500 mg of titanium compound (sensor 2) were exposed to an air stream, which contained 25 ppm of hexamethyldisiloxane (HMDS). The gas sensitivity for methane in mV/% LEL was determined at one-hour intervals in each case by applying 50% LEL methane to the air stream based on EN 60079.

It is recognized there that a drastic decrease in the sensitivity of the sensor for methane occurred within the shortest time without the filter material according to the present invention, and this had dropped to less than 10% of the initial sensitivity already after 2 hours. On the other hand, the sensitivity for methane remained almost unchanged for many hours in case of using the filter material according to the present invention in spite of the high concentration of HDMS used. A gas sensor with the filter material prepared in Example 1 is thus largely insensitive even to high concentrations of siloxanes.

While specific embodiments of the invention have been shown and described in detail to illustrate the application of the principles of the invention, it will be understood that the invention may be embodied otherwise without departing from such principles.

The invention claimed is:

1. A filter material for the selective removal of siloxanes from a gas, the filter material comprising a titanium compound, which is an organotitanate.

2. A filter material in accordance with claim 1, further comprising:
a compound, which can be obtained by partial or complete hydrolysis of an organotitanate.

3. A filter material in accordance with claim 1, wherein the organotitanate has the formula $Ti(OR)_4$, wherein at least one R is a hydrocarbon group with 1 to 10 carbon atoms and remaining R in each case independently represents hydrogen or a hydrocarbon group with 1 to 10 carbon atoms.

4. A filter material in accordance with claim 1, wherein the organotitanate is selected from the group consisting of tetramethyl titanate, tetraethyl titanate, tetra-n-propyl titanate, tetraisopropyl titanate, tetra-n-butyl titanate, tetra-tert-butyl titanate, tetra-n-hexyl titanate, di-isopropyl-di-n-butyl titanate, tetraphenyl titanate, titanium bis(triethanolamine)-diisopropoxide, titanium bis(triethanolamine)-di-n-butoxide, titanium (triethanolaminato)-isopropoxide, titanium bis(acetylacetonate)-diisopropoxide, titanium bis-(acetylacetonate)di-n-butoxide and mixtures thereof.

5. A filter material in accordance with claim 1, which contains 10 wt. % to 55 wt. % of titanium compound, calculated as titanium, in relation to an overall weight of the filter material.

6. A filter material in accordance with claim 1, further comprising a carrier.

7. A filter material in accordance with claim 6, wherein the carrier is a porous and fibrous carrier.

8. A filter material in accordance with claim 6, wherein the carrier is a porous particulate carrier and in the form of powder, granules, pellets or porous spheres.

9. A method for the production of filter material for the selective removal of siloxanes from a gas, the method comprising the steps of:
providing a titanium compound, which is an organotitanate or is a compound which can be obtained by hydrolysis of an organotitanate or is both an organotitanate and is a compound which can be obtained by hydrolysis of an organotitanate;
applying a solution of the organotitanate in a solvent to a carrier;
drying the carrier to provide filter material on the carrier; and
subjecting the filter material to conditioning wherein the conditioning is carried out by means of water vapor at 30° C. to 90° C.

10. A method according to claim 9, further comprising selectively removing siloxanes from a gas using the filter material.

11. A method according to claim 9, further comprising selectively removing siloxanes from a gas with the titanium compound.

12. A gas sensor, which comprises a filter material comprising a titanium compound, which is an organotitanate or is both an organotitanate and is a compound obtained by hydrolysis of an organotitanate.

13. A gas sensor in accordance with claim 12, wherein the quantity of titanium compound, calculated as titanium, is 0.1 mg/cm$^2$ to 100.0 mg/cm$^2$ in relation to a gas inlet area of the gas sensor.

14. A gas sensor in accordance with claim 12, wherein the titanium compound obtained by hydrolysis is obtained by a partial or complete hydrolysis of an organotitanate.

15. A gas sensor in accordance with claim 12, wherein the organotitanate has the formula $Ti(OR)_4$, wherein at least one R is a hydrocarbon group with 1 to 10 carbon atoms and remaining R in each case independently represents hydrogen or a hydrocarbon group with 1 to 10 carbon atoms.

16. A gas sensor in accordance with claim 12, wherein the organotitanate is selected from the group consisting of tetramethyl titanate, tetraethyl titanate, tetra-n-propyl titanate, tetraisopropyl titanate, tetra-n-butyl titanate, tetra-tert-butyl titanate, tetra-n-hexyl titanate, di-isopropyl-di-n-butyl titanate, tetraphenyl titanate, titanium bis(triethanolamine)-diisopropoxide, titanium bis(triethanolamine)-di-n-butoxide, titanium (triethanolaminato)-isopropoxide, titanium bis(acetylacetonate)-diisopropoxide, titanium bis-(acetylacetonate)di-n-butoxide and mixtures thereof.

17. A gas sensor in accordance with claim 12, wherein the titanium compound forms a part of filter material and the titanium compound, calculated as titanium, is 10 wt. % to 55 wt. % in relation to an overall weight of the filter material.

18. A gas sensor in accordance with claim 17 further comprising a porous carrier.

19. A filter material in accordance with claim 3, wherein each of the hydrocarbon groups is interrupted by one or more —O—, —NH—, —N= and/or —C(O)— and/or being substituted by one or more —OH and/or $NH_2$.

20. A filter material in accordance with claim 19, wherein two or three of the hydrocarbon groups are linked together forming a monocyclic or bicyclic ring and the organotitanate is a tetraalkyl titanate and/or tetraaryl titanate.

21. A filter material in accordance with claim 4, wherein the organotitanate is selected from the group consisting of tetraisopropyl titanate, tetra-n-butyl titanate and mixtures thereof.

22. A filter material in accordance with claim 7, wherein the carrier is a porous glass fiber mat.

* * * * *